United States Patent [19]

Clough et al.

[11] 4,164,570

[45] Aug. 14, 1979

[54] STABILIZED AQUEOUS CATECHOLAMINE SOLUTIONS

[76] Inventors: David Clough, 39, The Stewarts, Bishops Stortford, Hertfordshire CM21 2NU; Gary C.F. Ruder, 57 Greygoose Park, Harlow, Essex, both of England

[21] Appl. No.: 744,045

[22] Filed: Nov. 22, 1976

Related U.S. Application Data

[63] Continuation of Ser. No. 507,593, Sep. 20, 1974, abandoned.

[30] Foreign Application Priority Data

Sep. 24, 1973 [GB] United Kingdom ............... 44660/73
Sep. 24, 1973 [GB] United Kingdom ............... 44661/73

[51] Int. Cl.² .................... A61K 31/00; A61K 47/00; A61K 31/195; A61K 31/135
[52] U.S. Cl. .................................. 424/175; 424/319; 424/330
[58] Field of Search ................................ 424/175, 330

[56] References Cited

U.S. PATENT DOCUMENTS

| | | | |
|---|---|---|---|
| 2,744,938 | 5/1956 | Urban, Jr. ............................ | 260/582 |
| 3,187,050 | 6/1965 | Duggan et al. ...................... | 260/582 |
| 3,696,195 | 10/1972 | Crivellaro et al. .................. | 424/175 |

OTHER PUBLICATIONS

Moriyama et al., Chem. Abst. 77:118200(h) (1972).
Hecht et al., Chem. Abst. 75 80294(k) (1971).
Wilson et al., Textbook of Organic Medicinal and Pharmaceutical Chemistry, 4th Ed., (1962), pp. 390-392.
The Merck Index, 8th Ed., p. 397 (1968).
Irikura et al., Chem. Abst., 75 132984(g) (1971).
Stuzka et al., Chem. Abst. 75 45272(e) (1971).
Evans et al., Chem. Abst. 77 43326(t) (1972).
Oosterhuis, Chem. Abst. 57 14384(c) (1962).
Kuechle, Chem. Abst. 59 14482(c) (1963).
Hendley et al., Chem. Abst. 64 4128(e) (1966).

*Primary Examiner*—Albert T. Meyers
*Assistant Examiner*—D. W. Robinson

[57] ABSTRACT

An aqueous solution for treating glaucoma comprises 0.1-5.0% of a specially purified catecholamine e.g., epinephrine, 0.5-5.0% of a thiol, e.g., N-acetyl-L-cysteine, an acid compound unless the thiol is acid) to solubilize the catecholamine and a base e.g., $NH_4OH$ to bring the pH to 6.0-7.5, the solution being free from borate ions. The acid compound, if used can be e.g., lactic acid, which may be buffered with ammonium lactate, or ammonium dihydrogen phosphate; preferably alkali metal ions are avoided. Guanethidine or like compounds which potentiate epinephrine can also be present.

6 Claims, No Drawings

STABILIZED AQUEOUS CATECHOLAMINE SOLUTIONS

This is a continuation of application Ser. No. 507,593 filed Sept. 20, 1974 now abandoned.

This invention relates to aqueous solutions of catechol amines (dihydroxy phenylalkyl amines) and more especially of epinephrine, for use primarily in the treatment of open-angle glaucoma by application to the eye in drop form. It also relates to a method of preparing such solutions.

Epinephrine, and like biologically active catecholamines, are known to be useful in the treatment of open-angle glaucoma. However, any solution thereof to be instilled into the eye should ideally be near neutrality to avoid irritation to the surrounding tissues. Simple solutions of epinephrine have the disadvantage that at pH 7 or above the epinephrine base tends to precipitate. In highly acid solution epinephrine is more stable to oxidation but as the pH is raised to nearer 7, the epinephrine or like catecholamine, is readily attacked by oxygen giving progressively the red adrenochrome and brown melanin like products on further oxidation.

It has accordingly already been proposed for examnple in British Pat. No. 930452 to prepare aqueous epinephrine solutions adjusted to a suitable pH (stated to be 6.5–8.5) with sodium hydroxide, which solutions also contain sodium bisulphite, boric acid and 8-hydroxyquinoline together with a conventional antibacterial preservative. The sodium bisulphite antioxidant suffers from the disadvantage of reacting with the epinephrine to form an inactive derivative, but the use of boric acid, effectively as sodium borate slows down the rate of this undesirable side reaction and helps to solubilise the epinephrine, while 8-hydroxyquinoline stabilised the sodium bisulphite against oxidation.

Such a solution, is not particularly stable on storage under anaerobic conditions, and also does not possess good stability after first being opened for subsequent daily use.

A further proposal described in German patent application No. 2052991 uses as a stable antioxidant, instead of sodium bisulphite and 8-hydroxyquinoline, a mixture of ascorbic acid and a water-soluble pharmacologically tolerated thiolic stabilising agent, and states that a markedly improved resistance to oxidation is achieved. In practice the thiolic compound is usually N-acetyl-1-cysteine, and the pH is usually from 5.5 to 8.5, boric acid always being present and sodium hydroxide or sodium carbonate being used to adjust the pH as required. Under anaerobic conditions, however, the stability is not particularly good.

We have now discovered that improved results can be obtained over those of the prior art discussed above, as determined by stability either under anaerobic conditions (before the container is opened) or aerobic conditions (after opening) if a combination of two expedients is adopted. These are (i) the use of a purified form of catecholamine and (ii) the absence of borate ion. Moreover the use of ammonium salts only in the formulation, i.e., the avoidance of sodium or potassium hydroxides or carbonates as neutralizing bases and buffers, is preferable.

It is believed that purification of the catecholamine considerably reduces its normal content of heavy metal ion, especially ferric ions, and that the preferred subsequent use of ammonium salts only in the formulation prevents their reintroduction (i.e., as the normal trace contaminants of sodium or potassium salts or hydroxides) and it is further believed that this aids stability of the formulation. Moreover, in some way the absence of borate ion appears at least to help with anaerobic stability. However, the invention as defined below is not to be construed as dependent upon these hypotheses. It is moreover noteworthy that neither the British Pharmacopeia or the U.S. Pharmacopeia, mention the admissible levels of metal ion contaminant in epinephrine or other catecholamines.

In one aspect therefore the present invention provides an aqueous solution for topical application to living tissue and primarily to the eyes in the treatment of open-angle glaucoma, comprising from 0.1 to 5.0% by weight of a biologically active catecholamine in a purified form; from 0.5 to 5.0% by weight of a watersoluble pharmacologically tolerated thiolic stabilising agent; at least one acid or acid-reacting compound, unless the thiolic compound itself is suitably acidic, whereby the catecholamine is solubilised; and a base to bring the pH within the range of from 6.0 to 7.5, the solution being free from borate ions.

Preferably, the acid-reacting compound is an acid salt. The base may be an ammonium salt or ammonium hydroxide. Preferably moreover, the formulation is free from alkali metal ions.

While primarily the solution is intended for application to the eyes, it may also be applied to tissues of the nose, e.g., as inhaled droplets.

Usually the solution will contain an antibacterial preservative so that when a bottle is opened for use it does not become contaminated. Any conventional antibacterial agents, such as benzalkonium chloride, and/or other quaternary ammonium compounds, or biguanide compounds, may be used. Frequently, moreover, the solution will contain a thickening agent which is usually cellulosic in nature. Hydroxyethyl cellulose is preferred for this purpose since it gives an attractive clear solution which does not precipitate on heat sterilisation. A preferred viscosity is from 6 to 70 centipoises, e.g., about 15 cp.

From 0.1% to 2%, typically about 1%, by weight of the catecholamine is preferred. The degree of purification of the catecholamine necessary is generally such that the free base and aqueous solutions formed from it would be colourless, instead of the coloured somewhat impure material conventionally used hitherto. This is however best expressed that a typical catecholamine as used according to the invention shall preferably contain less than 1 part per million of heavy metal calculated as ferric ion. This is best achieved by making up the solution by mixing under nitrogen starting from the conventional crude base, and subsequently purifying it by normal chemical techniques to a colourless solution of the required impurity level. Such techniques can involve, for instance, absorption of impurities from acid solution on to activated charcoal with subsequent reprecipation of catecholamine using ammonium hydroxide.

The biologically active catecholamine may be one of the known catecholamines of biological activity. Such compounds may be expressed by the following formula:

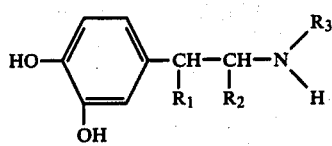

where $R_1$ can be hydrogen, hydroxyl, or oxo; $R_2$=hydrogen, methyl or ethyl, and $R_3$=hydrogen, methyl, ethyl, isopropyl, or

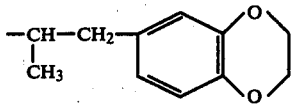

The preferred catecholamines are generally epinephrine isoprenaline and noradrenaline, and epinephrine is the most preferred compound.

From 0.5% to 2.0%, but typically 1.0% by weight or below is preferred for the thiolic compound. Suitable thiols may be selected from the classes of thiol-substituted carboxylic acids and esters and in particular thiol derivatives of α-amino acids, such as cysteine, its esters and its N-acyl derivatives, or thiol substituted polyols. Suitable examples are cysteine, methylcysteinate, N-acetyl-cysteine, α-mercaptol acetic acid, α-mercaptolpropionic acid, 1-thiosorbitol and 1-thioglycerol. A preferred compound is N-acetyl-L-cysteine, since this reacts acid and can thus be used in the absence of additional acid component to solubilise and stabilise the catecholamine. The base used is normally ammonium hydroxide.

In one form the acid added, if any, can be from 1.0 to 10.0% by weight of a simple hydroxycarboxylic acid preferably an alpha or beta hydroxy acid such as lactic, citric, malic or gluconic acid. The preferred acid is lactic acid which may be used in amounts of, e.g., about 2%. To facilitate holding the solution in the upper values of the pH range from pH 6.0 to pH 7.5 ammonium lactate may be present; this lactate may have been added as lactic acid and reacted in situ with excess NH$_4$OH.

In another form the solution contains as the acid component a phosphate, e.g., ammonium dihydrogen phosphate, or a phosphoric acid usually in amounts from 0.1 to 10% by weight, and preferably 0.1 to 0.5%. If N-acetyl cysteine is introduced as the acid component such a phosphate can have a buffering function and in such a case 4% by weight would be a usual upper limit. In this form of the invention a restricted pH range of pH 6 to 7, preferably from pH 6.2 to 6.7. e.g., about 6.5 is usual.

A very important optional feature of the present invention is to incorporate into the solution an effective amount of one or more adrenergic neurone blocking agents, which increases the pharmacological sensitivity to the adrenaline or like catecholamine. The solution of the invention is particularly adapted to include both the catecholamine and the adrenergic neurone blocking agent, and amounts of from 2% to 10% of the latter, preferably from 2% to 7% e.g. about 5% are preferred; if this is present it is possible to work with preferred catecholamine concentrations at the lower end of the range given, e.g., below 1%, and possibly down to 0.5 or 0.25%, for a useful degree of activity.

Typical adrenergic neurone blocking agents include bethanidine, but guanethidine of formula:

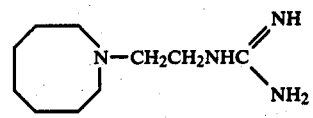

and its salts, especially its sulphate, is especially preferable.

While it is possible to use such adrenergic neurone blocking agents whatever the formulation, it is generally preferable if a system of lower ionic strength is used. Otherwise a formulation using for instance guanethidine may be hypertonic if a high concentration of buffer is present.

It will thus be apparent that two specific formulations are particularly valuable according to the invention.

The first of these is an aqueous solution containing from 0.1 to 2% by weight of epinephrine, in a purified form as described above; from 0.5 to 2% by weight of N-acetyl-L-cysteine; from 1.0 to 10% by weight of lactic acid; and sufficient ammonium hydroxide to neutralise the lactic acid and to give a pH within the range from 6.0 to 7.5. The second preferred composition according to the invention is an aqueous solution containing from 0.1 to 2% by weight of the purified epinephrine from 0.5 to 2% of N-acetyl-L-cysteine; from 0.1 to 0.5% by weight of ammonium dihydrogen phosphate; sufficient ammonium hydroxide to give a pH of 6.2 to 6.7; and from 2 to 7% of guanethedine.

While the invention in a major aspect provides aqueous solutions formulated as described above, it will be clear that, in other aspects it extends to (a) a method of treating a patient suffering from open-angle glaucoma in which such solutions are instilled into the eye, and also (b) to a method of stabilizing an aqueous catecholamine solution containing from 0.1 to 5% of a biologically active catecholamine wherein the catecholamine in a purified form as described above is added to from 0.5 to 5% by weight in aqueous solution of a water-soluble pharmacologically tolerated thiolic stabilizing agent, said solution containing at least one acid or acid-reacting compound unless the thiolic compound itself is suitably acidic, whereby the catecholamine is solubilised, and thereafter adding a base to bring the pH within the range of from 6 to 7.5, such solution being kept free from borate ions.

The invention will be further described with reference to the following examples in which all parts are expressed by weight unless otherwise specifically stated.

EXAMPLE 1

Purification of epinephrine by precipitation

An aqueous suspension of epinephrine (10% w/v), disodium edetate (1%) and sodium metabisulphite (1%) was adjusted to pH 4.5 under an atmosphere of nitrogen. Activated charcoal was added, the slurry stirred for 30 minutes and then removed by filtration. Epinephrine was reprecipitated from the filtrate by addition of ammonium hydroxide to pH 7.0, washed with water and isopropanol and finally dired in vacuo at 50° C. The purified epinephrine was stored in a well closed container under nitrogen at 5° C.

EXAMPLE 2

A formulation was made up containing:

| | |
|---|---|
| Epinephrine (purified) | 1.0 |
| N-acetyl cysteine | 1.0 |
| Natrosol 250 M (Hercules) | 0.4 |
| Benzalkonium chloride | 0.01 |
| Ammonium lactate | 4.0 |
| Ammonium hydroxide to | pH 6.5 |
| Distilled water | to 100 |

The solution was prepared by dissolving the N-acetylcysteine, epinephrine, antibacterial component and lactate in less than half the eventual quantity of water and under a nitrogen atmosphere. Then the Natrosol 250 M (a hydroxyethyl cellulose thickener) was dissolved in remaining half of the water and added, whereafter the solution was adjusted to the required pH with ammonia and made up to the volume.

Samples of the above solution were adjusted to different pH values with ammonium hydroxide and bubble tested by placing 100 ml of solution in a Drechsel bottle placing this in a water bath at 25° C. and bubbling air saturated with water vapour through the solution. End point was taken when the solution becomes deeply coloured.

| Results | pH | Bubble Time (days) |
|---|---|---|
| | 7.5 | 7 |
| | 7.0 | 14 |
| | 6.5 | 20 |
| | 6.0 | 20 |

Prior art formulations using bisulphite/borate/8-hydroxyquinoline as antioxidants, discoloured in less than one day in these drastic conditions, while prior art formulations using the N-acetyl cysteine/ascorbic acid borate system between pH 5.5 and 8.5 lasted something over 8 days before discolouring. The formulation according to the invention thus shows a marked improvement.

Anaerobic Ageing Tests

Samples of the solutions have been packed in ampoules under nitrogen and aged at 60° C. in order to accelerate possible degradation. The solutions have been assayed for NAC and epinephrine content with time. Results are given for solutions adjusted to pH 6.5.

The formulation of Example 2 gave the following results:

| Age in Weeks | Epinephrine | NAC |
|---|---|---|
| 0 | 1.07 | 0.97 |
| 2 | — | 0.89 |
| 4 | 0.85 | 0.82 |

Even after 8 weeks the solution was clear and colourless. A Similar solution, differing only in containing 2.0 parts of boric acid instead of the 4.0 parts of ammonium lactate gave the following results:

| Age in Weeks | Epinephrine Content % | NAC % |
|---|---|---|
| 0 | 0.99 | 0.98 |
| 2 | — | 0.85 |
| 4 | 0.60 | 0.66 |
| 8 | 0.46 | 0.48 |

In another test the prior art product using ascorbic acid and N-acetyl-cysteine when stored at 60° C. discolours within 4 weeks. This does not occur with the above solutions. It is known that ascorbic acid can decompose anaerobically to coloured breakdown products and the decomposition is accelerated by borate ions; the products of the invention are free from this disadvantage.

Solutions made up as in this and subsequent Examples should be packaged in a manner preventing ingress of oxygen so that they remain colourless throughout a normal storage life.

EXAMPLE 3

A like formulation to that of Example 2 but containing guanethidine was made up to the following concentration in parts by weight.

| | |
|---|---|
| Guanethidine Sulphate | 3.0 |
| Epinephrine | 0.5 |
| N-acetylcysteine | 0.5 |
| Ammonium lactate | 4.0 |
| Natrosol 250 M | 0.4 |
| Benzalkonium Chloride | 0.01 |
| Ammonium Hydroxide | to pH 7.0 |
| Distilled water | to 100 |

EXAMPLE 4

Formulations were made up containing:

| | 1 | 2 | 3 | 4 | (Comparative Test) 5 |
|---|---|---|---|---|---|
| Epinephrine | 1 | 1 | 1 | 1 | 1 |
| N-acetylcysteine (NAC) | 1 | 1 | 1 | 0.5 | 1 |
| Natrosol 250 M | 0.4 | 0.4 | 0.4 | 0.4 | 0.4 |
| Benzalkonium chloride | 0.01 | 0.01 | 0.01 | 0.01 | 0.01 |
| Ammonium dihydrogen phosphate | — | 0.4 | 2.0 | 2.0 | — |
| Ammonium hydroxide to | pH 6–7 | pH 6–7 | pH 6–7 | pH 6–7 | pH 6–7 |
| Distilled water | to 100 | to 100 | to 100 | to 100 | to 100 |
| Boric acid | | | | | 2.0 |

Such solutions were prepared and tested as described in Example 2.

Results were as follows (a) Aerobic (bubble) test

-continued

| | pH | Bubble Time (days) |
|---|---|---|
| Solution 4 | | |
| Epinephrine + phosphate (2.0) + NAC (0.5)) | 7.0 | 15 |
| | 6.5 | 18 |
| | 6.0 | 18 |
| Solution 1 | | |
| (Epinephrine + NAC (1/0)) | 7.0 | 14 |
| | 6.5 | 23 |
| | 6.0 | 23 |

(b) Anaerobic Tests

| | Age (Weeks) | Epineprhine Content % | NAC % |
|---|---|---|---|
| Solution 1 | | | |
| Epinephrine + NAC (1.0)) | 0 | 0.99 | 0.97 |
| | 4 | 0.85 | 0.80 |
| | 8 | 0.67 | 0.64 |
| Solution 5 | | | |
| Epinephrine + NAC (1.0) | 0 | 0.99 | 0.98 |
| + Borate (2.0)) | 2 | — | 0.85 |
| | 4 | 0.60 | 0.66 |
| | 8 | 0.46 | 0.48 |

By comparison of results obtained in the Solution 1 and Solution 5, it will be seen that epinephrine+NAC, without any other material has superior anaerobic ageing characteristics both for epinephrine and NAC content. It may be therefore that the addition of other material increases the level of metal ion or other contamination. Metal ions are known to catalyse the rate degradation both of epinephrine and of thiol.

EXAMPLE 5

A like formulation but containing guanethidine was made up to the following concentration in parts by weight.

| | |
|---|---|
| Guanethidine Sulphate | 5.0 |
| Epinephrine | 0.5 |
| N-acetyl cysteine | 1.0 |
| Ammonium dihydrogenphosphate | 0.2 |
| Natrosol 250m | 0.4 |
| Benzalkonium Chloride | 0.01 |
| Ammonium Hydroxide | to pH 6.5 |
| Distilled water | to 100 |

EXAMPLE 6

A formulation was made up containing 1% purified epinephrine 1% NAC and 2.0% ammonium lactate, the pH being further adjusted to different values by ammonium hydroxide. Anaerobic aging data were as follows.

| | 60° C. | | | | | 40° C. | | | | 20° C. | | |
|---|---|---|---|---|---|---|---|---|---|---|---|---|
| Age (weeks) | 0 | 1 | 4 | 8 | 12 | 1 | 4 | 8 | 12 | 26 | 1 | 12 | 26 |
| Epinephrine % | 1.07 | | 0.83 | 0.65 | 0.55 | | 1.02 | 1.00 | 1.00 | 0.99 | | 1.10 | 1.18 |
| NAC % | 1.01 | 0.83 | 0.62 | 0.50 | 0.40 | 0.89 | 0.86 | 0.81 | 0.77 | 0.79 | 0.93 | 0.92 | 0.88 |
| pH | 6.7 | 6.5 | 6.3 | — | 6.2 | 6.6 | 6.5 | — | 6.6 | 6.5 | 6.7 | 6.7 | 6.7 |

In the bubble test as described above such solutions lasted over 400 hours without discoloration, compared to 16 hours for neutral epinephrine eye drop solution and 192 hours for a prior art epinephrine borate—0.5% NAC—0.5% ascorbic acid system of similar pH.

EXAMPLE 7

A formulation was made up containing 0.5% purified epinephrine, 1% NAC, 5% quanethidine sulphate and sufficient ammonium dihydrogen phosphate base to give the required pH values.

Anaerobic aging data were as follows:

| | 60° C. | | | | | 40° C. | | 20° C. | |
|---|---|---|---|---|---|---|---|---|---|
| Age (weeks) | 0 | 2 | 4 | 8 | 12 | 12 | 26 | 12 | 26 |
| Epinephrine % | 0.38 | | 0.25 | 0.16 | 0.10 | 0.35 | 0.35 | 0.38 | 0.37 |
| NAC % | 0.92 | 0.84 | 0.8 | 0.66 | 0.60 | 0.9 | 0.89 | 0.84 | 0.91 |
| Guanethidine SO4 % | 4.6 | | 4.5 | 4.5 | 4.6 | 4.6 | 4.6 | 4.6 | 4.5 |
| pH | 6.6 | | 6.6 | 6.6 | 6.7 | 6.6 | 6.6 | 6.6 | 6.6 |

In the bubble test such solutions lasted 240 hours before discoloration.

EXAMPLE 8

Biological activity

Epinephrine has both a mydriatic and hypotensive action in the eye. The mydriatic effect was measured in rabbits eyes by measuring the pupil diameter after drug treatment. Neutral epinephrine eye drops BPC were used as control. Results are given as the mean of eight observations.

| Time in minutes | | | | | |
|---|---|---|---|---|---|
| Mean pupil diameter | 5.58 | 6.38 | 6.36 | 6.14 | } Epinephrine + |

| Time in minutes | | | | | |
|---|---|---|---|---|---|
| Standard error of mean | 0.08 | 0.22 | 0.19 | 0.18 | lactate + NAC |
| Mean pupil diameter | 6.26 | 6.47 | 6.83 | 6.61 | Neutral epinephrine eye drops BPC |
| Standard error of mean | 0.08 | 0.15 | 0.26 | 0.17 | |

The 't' test showed that the lactate formula did not differ significantly from neutral epinephrine BPC (P>0.3).

The hypotensive action was determined by measuring the pressure drop in treated rabbit eyes. Preliminary experiments indicated that formulations containing 1% epinephrine produced nearly maximal responses; 0.25% solutions were therefore prepared which were otherwise identical to the 1% solutions. The solutions were compared against 2.5% epinephrine bitartrate a standard maximal concentration. The mean maximum observed pressure falls in 8 rabbits were as follows:

|  | 0.25% epinephrine in phosphate base | 0.25% epinephrine in lactate base | 2.5% epinephrine bitartrate |
|---|---|---|---|
| Mean (mm Hg) | 3.51 | 3.61 | 5.13 |
| Standard error of mean | 0.38 | 0.26 | 0.52 |

It was therefore concluded that the phosphate and lactate formulations were equally potent hypotensives.

The potentiation of the hypotensive action of epinephrine by guanethidine is best shown in rabbits by a seven day pretreatment of the rabbit eye with a 5% solution of guanethidine sulphate followed by instillation of the epinephrine. The action of guanethidine is accumulative and the pre-treatment assures maximum potentiation.

The mean maximum observed pressure falls in 8 rabbits were as follows:

| 0.25% epinephrine bitartrate no pre-treatment | 1.2 mm ± 0.4 |
|---|---|
| 0.25% epinephrine bitartrate with pre-treatment | 4.0 mm ± 0.8 |

We claim:

1. A borate-free aqueous solution for the topical application to the eyes in the treatment of open-angle glaucoma, said solution comprising from 0.1 to 2.0 percent of epinephrine, said epinephrine containing less than 1 part per million of heavy metal calculated as ferric ion, from 0.5 to 2.0 percent of N-acetyl cysteine, said N-acetyl cysteine being present in at least equimolar proportion to the epinephrine whereby it solubilizes the epinephrine as well as stabilized the solution, ammonium hydroxide in an amount sufficient to give a pH of less than 7.5 and an ammonium buffer, said solution having a pH in the range of from 6.0 to 7.5.

2. An aqueous solution as described in claim 1 further containing from 1.0 to 10 percent by weight of lactic acid.

3. An aqueous solution as claimed in claim 1 wherein a cellulosic thickening agent is present in an amount sufficient to provide a solution viscosity of from 6 to 70 centipoises.

4. A borate-free aqueous solution for the topical application to the eyes in the treatment of open-angle glaucoma, said solution comprising from 0.1 to 2.0 percent of epinephrine, said epinephrine containing less that 1 part per million of heavy metal calculated as ferric ion, from 0.5 to 2.0 percent of N-acetyl cysteine, said N-acetyl cysteine being present in at least equimolar proportion to the epinephrine whereby it solubilizes the epinephrine as well as stabilizes the solution, from 2 to 7 percent of guanethidine as an adrenergic neurone blocking agent, ammonium hydroxide in an amount sufficient to give a pH of less than 7.5 and an ammonium buffer, said solution having a pH in the range of from 6.0 to 7.5.

5. An aqueous solution as described in claim 4 further containing from 0.1 to 0.5 percent by weight of ammonium dihydrogen phosphate.

6. An aqueous solution as described in claim 5 wherein said solution has a pH in the range of from 6.2 to 6.7.

* * * * *

UNITED STATES PATENT AND TRADEMARK OFFICE
CERTIFICATE OF CORRECTION

PATENT NO. : 4,164,570

DATED : August 14, 1979

INVENTOR(S) : David Clough and Gary C. F. Ruder

It is certified that error appears in the above—identified patent and that said Letters Patent is hereby corrected as shown below:

In column 1, following the name and address of the inventor, should be added:
    On the title page insert:
-- Assignee: [73]    Smith & Nephew Pharmaceuticals Limited, Welwyn Garden City, Hertfordshire, England --.

Signed and Sealed this

Twenty-seventh Day of January 1981

[SEAL]

Attest:

RENE D. TEGTMEYER

Attesting Officer

Acting Commissioner of Patents and Trademarks